(12) United States Patent
Goodall et al.

(10) Patent No.: US 11,638,731 B2
(45) Date of Patent: *May 2, 2023

(54) MEDICAL COMPOSITIONS WITH OMEGA-3 CONTAINING EXCIPIENTS

(71) Applicant: Nooter/Eriksen, Inc., St. Louis, MO (US)

(72) Inventors: Brian L. Goodall, Bretby (GB); Dmitry Kuklev, Ann Arbor, MI (US); Glen L. Bostick, Columbia, IL (US)

(73) Assignee: Nooter/Eriksen, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/718,045

(22) Filed: Apr. 11, 2022

(65) Prior Publication Data

US 2022/0226404 A1 Jul. 21, 2022

Related U.S. Application Data

(63) Continuation-in-part of application No. 16/953,978, filed on Nov. 20, 2019, now Pat. No. 11,298,387.

(51) Int. Cl.
| | |
|---|---|
| *A61K 31/00* | (2006.01) |
| *A61K 36/05* | (2006.01) |
| *A61K 45/06* | (2006.01) |
| *A61K 47/54* | (2017.01) |

(52) U.S. Cl.
CPC .............. *A61K 36/05* (2013.01); *A61K 45/06* (2013.01); *A61K 47/543* (2017.08)

(58) Field of Classification Search
CPC .................................................. A61K 36/05
See application file for complete search history.

(56) References Cited

U.S. PATENT DOCUMENTS

| | | |
|---|---|---|
| 8,115,022 B2 | 2/2012 | Kale |
| 8,153,137 B2 | 4/2012 | Kale |
| 8,318,963 B2 | 11/2012 | Kale et al. |
| 8,569,531 B2 | 10/2013 | Kale |
| 8,591,912 B1 | 11/2013 | Kadam et al. |
| 8,753,707 B2 | 6/2014 | Fichtali et al. |
| 8,828,447 B2 | 9/2014 | Soerensen et al. |
| 2017/0035719 A1 | 2/2017 | Waibel et al. |
| 2017/0119005 A1 | 5/2017 | Piechocki et al. |
| 2018/0289735 A1* | 10/2018 | Hill ........................ A23K 20/10 |

FOREIGN PATENT DOCUMENTS

| | | |
|---|---|---|
| RU | 2512375 C1 | 4/2014 |
| UZ | 4370 C | 7/2011 |
| WO | 20030015518 A1 | 2/2003 |
| WO | 2010027258 A1 | 3/2010 |
| WO | 20140105576 A1 | 7/2014 |
| WO | 2019095280 A1 | 5/2019 |
| WO | 2019201478 A1 | 10/2019 |

OTHER PUBLICATIONS

Schultz, Hank, New Algae Player Debuts With Highly Refined EPA Ingredient, William Reed Business Media Ltd, Dec. 19, 2018 (https://www.nutraingredients-usa.com/Article/2018/12/19/New-algae-player-debuts-with-highly-refined-EPA-ingredient#).
Search Report to corresponding PCT/US2020/061561 dated Aug. 19, 2021.
Written Opinion to corresponding PCT/US2020/061561 dated Aug. 19, 2021.

* cited by examiner

*Primary Examiner* — Qiuwen Mi (74) *Attorney, Agent, or Firm* — Sandberg Phoenix & von Gontard, PC (57) ABSTRACT

A composition comprising a concentration of total lipids, wherein at least 20% of the total lipids concentration by weight % comprises a polar lipids fraction, with greater than about 30% by weight % of the polar lipids fraction comprising glycolipids, and wherein the composition comprises no greater than 4% of its weight % as chlorophyll concentration, and formulations and medical compositions including the lipids-containing composition.

48 Claims, 4 Drawing Sheets

MEDICAL COMPOSITIONS WITH OMEGA-3 CONTAINING EXCIPIENTS

REFERENCE TO RELATED APPLICATIONS

This application is a Continuation-in-part application of U.S. application Ser. No. 16/953,978 filed Nov. 20, 2020, which is incorporated herein by reference.

STATEMENT REGARDING FEDERALLY SPONSORED RESEARCH OR DEVELOPMENT

Not Applicable.

BACKGROUND

Safe, readily available, and synergistic excipients are in high demand today in both the pharmaceutical and nutraceutical industries, where the performance of medical compositions is held to high standards. Excipients comprise all ingredients in a medical composition that are not considered to be 'active pharmaceutical ingredients' (APIs) or otherwise active ingredients. Despite traditionally being considered 'inactive' ingredients, excipients are now understood to be potential determinants of dosage form performance, affecting not only the color, flavor, and vehicle form of e.g. a parenteral medical composition, but also factors including, but not limited to, the stability, bioavailability, or patient acceptability of the active ingredients with which they are formulated. Moreover, excipients can be found to comprise, e.g., up to 90% of medications, and their implementation is monitored by the US Pharmacopeia (USP) and regulated by international and national organizations such as the Food and Drug Administration (FDA). Thus, there is great need for medical dosage forms comprising safe, beneficial excipients that are easily and inexpensively manufactured from readily available sources.

One such excipient ingredient is fatty acids, such as Omega-3 fatty acids. Omega-3 fatty acids can be employed in enteric coatings, which are the coatings of capsules, tablets, and other orally-ingested medical compositions. Control of enteric coating composition can influence both the location and rate of active ingredient release in the digestive tract. These compounds can also be found in formulations of e.g. topical creams, suppositories, and soaps.

Omega-3 fatty acids, also referred to as long chain Omega-3 oils, are vital to human health and deficits in them can have serious, negative health impacts. These range from developmental deficiencies in brain and neural networks to our cardiovascular health, and more. Even when employed as excipients, research has shown Omega-3 oils can act as cancer inhibitors. Oleic acid, for example, when employed alongside Herceptin for treatment of breast cancer, performs not only as a drug delivery vehicle but actually inhibits the breast cancer gene. Other Omega-3 acids are recognized to have anti-tumor activity and cardiovascular benefits, respectively. Omega-3 oils are in high demand today due to supply limitations in aquaculture, fisheries, and other marine sources, at latest report, being able to supply only approximately 0.8 million tons of Omega-3 fatty acids per year for human consumption. This is well below the current human nutritional demand of 1.4 million tons required to supply the global population with 500 mg Omega-3 fatty acids daily and will be further exacerbated by population growth. Omega-3 fatty acids deficiencies have been observed worldwide, and particularly affect populations located in North America, central Europe, the Middle East, India, Brazil, and the United Kingdom, with regional and socioeconomic differences seen within these countries.

There are three major Omega-3 fatty acids found in nature. Alpha linoleic acid (ALA), with 18 carbons and 3 double bonds, can be found, e.g., in flax seeds, soybean oil and olives. Docosahexaenoic acid (DHA) with 22 carbons and 6 double bonds, and Eicosapentaenoic acid (EPA), with 20 carbons and 5 double bonds, are only produced in aquatic species (algae) and can be extracted from krill or fish that eat the algae, or from the algae themselves. Given the thousands of naturally-occurring and easily cultivatable strains of microalgae, it is possible to select for particular fatty acids by selecting for the corresponding microalgae strain(s).

"Working algae", i.e., algae grown using sunlight or artificial light using photosynthesis comprise mostly polar lipids, which fall into the categories of glycolipids and phospholipids. By their nature, these species have hydrophobic tails and a polar (hydrophilic) head—i.e., they are essentially exotic natural detergents. These materials have exceptionally high bioavailability, and thus, readily enter the human bloodstream to deliver the above-mentioned health benefits. Various of these valuable materials have proven not found to be naturally produced in other sources, such sources may be of questionable sustainability, or have proven to be difficult to feasibly access. Moreover, extracting them from microalgae efficiently and in their pure, natural, bioavailable form, has not previously been effectively accomplished in a commercially successful manner, as existing commercial products have been hampered by an unattractive appearance, odor, and texture. While having a higher bioavailability, algal extracts have traditionally included components which give the oil extracted from them an overall, very dark, nearly black-ish, appearance, and a highly viscous feel, making them resemble an unattractive tar-like black solid which remains relatively low in concentrations of the Omega-3 oils themselves.

Additionally, existing crude products have previously not been able to be fully or adequately analyzed and characterized. Indeed, despite decades of study, a fully characterized mass balance has not been accomplished or published without either reporting inclusions of high levels (e.g., up to 10% or more) "unknowns" or "unidentified" materials, or by reporting results only "by difference" and putting such essentially uncharacterized materials in a bucket labelled simply as "carbohydrates", for example. This is especially undesirable in the case of nutraceutical and pharmaceutical products.

In summary, highly bioavailable, high concentration Omega-3 containing, EPA-containing, high in polar lipids, especially glycolipids composition, which presents as a low viscosity, low chlorophyll content light amber to dark amber colored oil for use in nutraceutical and pharmaceutical products, particularly as excipients in the dosage forms of such products, the contents of which are fully, or nearly fully characterized, is currently unavailable, yet highly desirable. Moreover, a method to obtain such highly desirable compositions directly from plentiful, highly sustainable algae sources, would be ideal.

SUMMARY

The present disclosure describes a solution to the above problems by providing nutritionally and medically helpful, prophylactic and/or therapeutic dosage forms comprising low-viscosity, low chlorophyll content omega-3- and EPA-containing excipients. All dosage forms of the present inventions present as combinations of active ingredient and excipients, and can be produced from the specified materials by conventional methods of processing and manufacture known in the art. Materials for dosage forms utilizing such excipients in the present inventions are sourced by utilizing a liquid-liquid separation process to extract oil extracts from microalgal biomass. The crude extract is then fractionated into clean, well-characterized fractions, e.g., polar lipids, polysaccharides, and carotenoids, with high efficiency and very high recovery. By virtue of the innovative fractionation process of the disclosure, a full mass balance of the oil extract, and of the entire algal biomass, is now possible. Careful portioning of the desired components into excipient formulations permits their incorporation into medical compositions. Thus, in another aspect, omega oil-rich medical compositions and the processes for generating them are provided.

In one embodiment, the disclosed process includes a method for production of a low chlorophyll content oil composition comprising the steps of obtaining an algal paste; extraction of the algal paste with a polar solvent such as an alcohol like ethanol to form an extract of algal lipids; extraction of the obtained extract with, e.g., an organic solvent such as the hydrocarbons hexane or heptane, to separate the fraction of non-polar lipids, transferring the, e.g., alcohol layer containing pigments and polar lipids to a further stage of processing; adding water to the, e.g., alcohol layer extracted, e.g., with heptane, and then its sequential extraction with, e.g., heptane, to extract the pigment fraction and separating out the polar lipid fraction. Polar lipids can then be obtained from the fraction containing them by evaporation, and pigments can also be obtained by evaporation of the fraction containing them.

In an alternative embodiment, the disclosed process includes a method for production of a low chlorophyll content oil composition comprising the steps of obtaining an algal biomass which includes both polar and non-polar lipid fractions and also has a chlorophyll concentration. The method further includes using polarity characteristics of the polar and non-polar lipid fractions to segregate polar from non-polar components in the algal biomass, including substantially segregating the chlorophyll concentration with the non-polar lipid fraction. Additional steps include bleaching out substantially all the chlorophyll concentration from the non-polar containing fraction; and re-combining the polar and non-polar lipid fractions to produce the low chlorophyll-content LC-PUFA oil composition.

The above process embodiments produce an attractive composition for use in both the nutraceutical and pharmaceutical fields, particularly in terms of reduced opacity and viscosity.

In a related embodiment, a method of fractionating and clarifying algal paste into its clean, precisely characterized components of Liquid Extracted Biomass, i.e., the residual post-extraction biomass ("LEA"), polar lipids, pure neutral lipids, chlorophyll, polysaccharides, carotenoids with high recovery of the total, and reporting a full algal biomass balance, is provided. The method comprises the steps of obtaining an algal paste; extraction of the algal paste with a polar solvent such as an alcohol like ethanol to form, e.g., an alcoholic extract of algal lipids; extraction of the obtained, e.g., alcoholic extract with, e.g., an organic solvent such as the hydrocarbons hexane or heptane, to separate the fraction of non-polar lipids, transferring the, e.g., alcohol layer containing pigments and polar lipids to a further stage of processing; adding water to the, e.g., alcohol layer extracted, e.g., with heptane, and then its sequential extraction with, e.g., heptane, to extract the pigment fraction and separating out the polar lipid fraction The disclosure further relates to a bioavailable, LC-PUFA-, Omega-3-, EPA-, polar lipids- and glycolipids/phospholipids-rich composition especially suitable for use in nutraceutical and pharmaceutical compositions, which can be considered as health or medical compositions, and as having other valuable end products. Starting material for this composition may be derived from algae as described herein. In one embodiment, a composition is disclosed including a polar lipids fraction of a concentration of total lipids of at least 20% of the total lipids by weight %; wherein the polar lipids fraction comprises at least 40% glycolipids by weight; and wherein the composition comprises no greater than 4% of its weight % as a chlorophyll concentration.

The composition, prepared as described above, with its total lipids having a fraction of at least 20 wt. % polar lipids, and its polar lipids having a fraction of at least 40 wt. % glycolipids, but the composition having less than a 4 wt. % chlorophyll fraction, may further include formulations with additive non-polar lipids and/or nutraceutical oils such as DHA, or other beneficial additives as more fully described below, which also assist in providing for certain beneficial combinations of a more bioavailable, nutrient rich, lighter color, lower viscosity, oil.

These features and other features of the present disclosure will be discussed in further detail in the following detailed description.

DETAILED DESCRIPTION

The following detailed description illustrates the claimed disclosure by way of example and not by way of limitation. This description will clearly enable one skilled in the art to make and use the claimed disclosure, and describes several embodiments, adaptations, variations, alternatives and uses of the claimed disclosure. Additionally, it is to be understood that the claimed disclosure is not limited in its application to the details and compositions specifically set forth in the following description or illustrated by means of the figures. The claimed disclosure is capable of other embodiments and of being practiced or being carried out in various ways. Also, it is to be understood that the phraseology and terminology used herein is for the purpose of description and should not be regarded as limiting.

As used herein, the term "polar lipids" means amphiphilic lipids with a hydrophilic head and a hydrophobic tail. Examples of polar lipids include phospholipids and glycolipids.

As used herein the term "non-polar lipids" means fatty molecules wherein the charge distribution is largely evenly distributed, and the molecules do not have positively and negatively charged ends. Examples of non-polar lipids include triglycerides of the various fatty acids in the oil (e.g., EPA, palmitoleic acid and others, including mixtures thereof such as triglycerides (TAGs) comprising variations or combinations of such fatty acids).

As used herein, the acronyms "EPA" and "DHA" refer to eicosapentaneoic acid and docosahexaenoic acid, respectively, as well as the salt and ethyl ester forms of each compound. In its naturally-occurring acid form, EPA is a twenty-carbon unsaturated chain culminating in a carboxylic acid functional group. However, one of ordinary skill in the art appreciates that natural variants of this acidic form include an alkaline salt, in which the deprotonated carboxylic acid is stabilized by a counter anion, and an ethyl ester, in which two more carbons are singly covalently bonded to the spa-hybridized oxygen so as to result in an ester. In the case of the ethyl ester form, then, EPA has twenty-two carbons. Similarly, DHA in its acidic form is a twenty-two-carbon unsaturated chain culminating in a carboxylic acid functional group, and is understood to have natural variants including the alkaline salt and ethyl ester form. In the ethyl ester form, consequently, DHA has twenty four carbons. Alkaline salt forms of eicosapentaneoic acid and docosahexaenoic acid may manifest spontaneously as a result of particular chemical environments in which they are present. The transformation to the ethyl ester variants is similarly facile, and these variants are also used as medicants to treat, for example, high blood triglyceride levels. Any use of the acronyms "EPA" and "DHA" in the present application should not be construed to exclude the alkaline salt or ethyl ester variants of either compound unless their exclusion is made explicit.

As used herein, the term "medical composition" refers to a composition, meant to be taken by a patient for therapeutic, curative, or prophylactic purposes, comprising active and inactive ingredients. Medical compositions whose active ingredients are primarily intended to aid in nutrition, they are referred to as 'nutraceuticals.' Medical compositions whose active ingredients are primarily pharmacological drug products, they are referred to as 'pharmaceuticals.'

As used herein, the term "dosage form" refers to the form of the medical composition by which its components are to be administered. Dosage forms include active and inactive ingredients. Dosage forms can be liquid, solid, or gaseous, and can include, but are not limited to, tablets, pills, capsules, wafers, lozenges, liquid solutions, et cetera. Dosage forms may be "swallowable," referring to their parenteral use, and in addition may be "chewable," in that their ingestion is substantially aided by mastication. Dosage forms may also be "dissolvable," wherein their preferred route of ingestion is via first dissolution in an aqueous medium such as water.

As used herein, the terms "inactive" and "excipient" refer to any and all compounds and elements that are not the active ingredient of a composition. The definition herein follows that adopted by the Food and Drug Administration (FDA) as described in the Code of Federal Regulations (CFR). The regulation of excipients is such that they must meet stringent requirements for purity and toxicity. Excipients should not be construed to necessarily have no therapeutic benefit. Excipients such as formed from the omega-3 oil compositions in the present inventions may have synergistic and/or individually therapeutic effects as a result of their inclusion in the dosage form. The use of one or more excipients belonging to particular recognized class (e.g., fillers, softeners, dyes, coating agents) does not preclude the use of excipients of another recognized class within the same embodiment of the present inventions.

As used herein, the term "active ingredient" thus also refers to the definition adopted by the FDA and as described in the CFR. By way of providing a descriptive and non-limiting summary of the term, and active ingredient is meant to refer to any substance intended to directly provide curative, mitigative, therapeutic, or any other pharmaceutical or nutraceutical effect.

As used herein, the term "antioxidant" refers to any substance that stops, inhibits, or otherwise interferes with the chemical process of oxidation and therefore its deleterious effects. Antioxidants comprise a wide range of compounds whose identity and common use are known to those of ordinary skill in the art.

As used herein, the term "vitamin" refers to any organic molecule or set of chemically related molecules considered by those of ordinary skill in the art to be essential micro-nutrients required for proper metabolic function in a mammalian organism. Such nutrients generally cannot be synthesized in sufficient quantities within the organism and therefore, must be obtained through diet. For purposes of the claimed invention, most major health organizations consider the following list to comprise known vitamins essential to human health: vitamin A, vitamin B1, vitamin B2, vitamin B3, vitamin B5, vitamin B6, vitamin B7, vitamin B9, vitamin B12, vitamin C, vitamin D, vitamin E, vitamin K, and, in some instances, choline. Note that the foregoing list is intended to be illustrative rather than limiting. Note that particular vitamin names refer to "vitamers," or groups of related chemical compounds, organized under a single name. For example, the term "vitamin A" refers to a vitamer comprising trans-retinol and trans-retinyl esters. Herein, the term for a vitamin as listed above comprises all known compounds within the associated vitamer.

As used herein, the term "mineral" refers to essential nutrients that are also chemical elements, excluding oxygen, carbon, hydrogen, and nitrogen. The major mineral nutrients are understood to be calcium, phosphorus, potassium, sodium, and magnesium, but can further comprise elements with trace presence in the human diet, comprising sulfur, iron, chlorine, cobalt, copper, zinc, manganese, molybdenum, iodine, and selenium.

To produce the disclosed embodiments of clarified compositions of an algal biomass, an algal paste, which presents as a dark green or even black, highly viscous oil can be obtained using standard steps know by those of ordinary skill in the industry. See, e.g., the production of the algal paste and useful varieties of algae employable, as described in U.S. Pat. No. 8,591,912 B1 (hereinafter "Kadam and Goodall"), incorporated herein by reference and additionally discussed herein.

Procedures for obtaining the algal biomass extract, and starting algae and extraction procedures for preparing the algal biomass can include the following steps, as part of a liquid-liquid extraction:

Obtain or prepare an algal biomass such as an algal paste from an appropriate algal species suitable for producing such a target algal biomass. In general, microalgae can be harvested by conventional means (including, but not limited to filtration, air flotation and centrifugation) and the algal paste generated by concentrating the harvested microalgae to the desired weight % of solids. In certain embodiments, the microalgae used with the methods of the invention are members of one of the following divisions: Chlorophyta, Cyanophyta (Cyanobacteria), and Heterokontophyta. In certain embodiments, the microalgae used with the methods of the invention are members of one of the following classes: Bacillariophyceae, Eustigmatophyceae, and Chrysophyceae. In certain embodiments, the microalgae used with the methods of the invention are members of one of the following genera: *Nannochloropsis, Chiarella, Dunaliella, Scenedesmus, Selenastrum, Oscillatoria, Phormidium, Spirulina, Amphora, Trachydiscus* and *Ochromonas*. Non-limiting examples of microalgae species that can be used with the methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris fo. tertia, Chlorella vulgaris* var. *vulgaris fo. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii, Trachydiscus*, and *Viridiella fridericiana*.

Preferred algal species are those, e.g., rich in LC-PUFA oil sources. Exemplary of such algae strains are strains from *Nannochloropsis* or *Chlorella* algal varieties.

The algal paste or other suitable form of algal biomass can be processed as follows: extract, e.g. with a polar solvent such as an alcohol, including, ethyl alcohols to form, e.g., an alcoholic extract of algal lipids with a low water content (forming, e.g., an ethanolic extract of *Nannochloropsis* lipids (hereinafter referred to for brevity as "EEN"); extract the obtained EEN with, e.g., an organic solvent such as the hydrocarbons hexane or heptane to separate out the fraction of non-polar lipids (e.g., triglycerides, waxes, carotenes), thus forming a "non-polar lipid fraction" (F #1 of FIG. 1) in the heptane layer. The alcohol layer containing pigments and polar lipids can be transferred to a further stage of processing. See FIG. 1. Other polar solvents such as carbon dioxide or carbon dioxide ethanol mixes may be considered.

Figure 1:
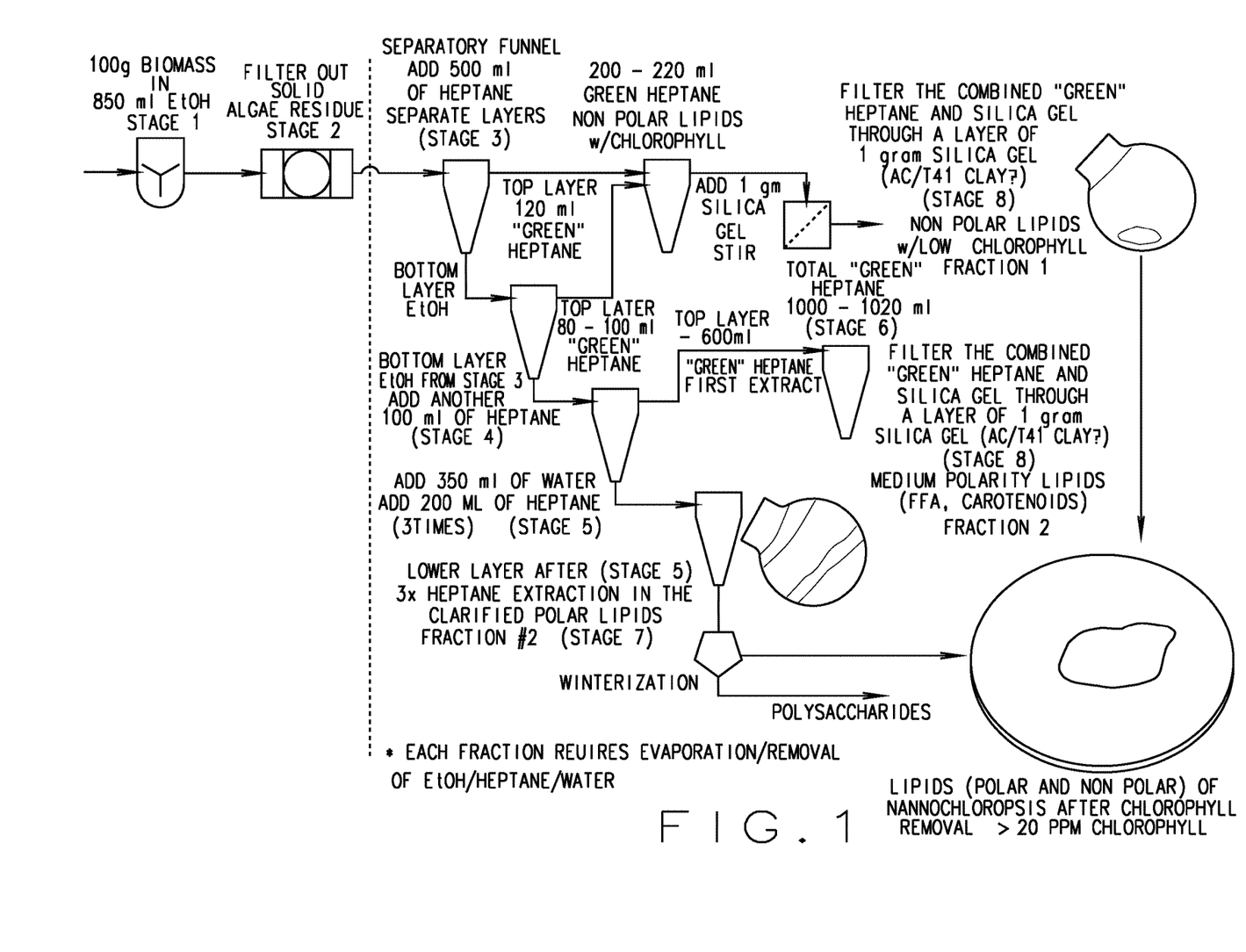
FIG. 1 discloses a schematic diagram of extraction process steps for an exemplary method of preparation of the oil of an embodiment of the disclosure.
Figure 2:
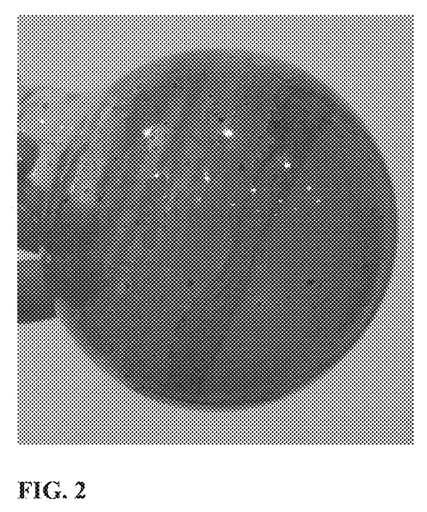
FIG. 2 is a photographic depiction of an embodiment of a composition of the disclosure made according to the exemplary method as set forth in FIG. 1, having a desired target LC-PUFA-, polar lipid-, Omega-3-, EPA- and glycolipid-rich and chlorophyll-reduced concentration, with bioavailability, color and viscosity of a desired oil composition, embodiments of which are disclosed herein.

The next stage of processing can involve adding water to the polar solvent layer extracted, e.g., with heptane and then its sequential extraction with, e.g., heptane, to extract the pigment fraction (see FIG. 1, heptane layer, F #3) and separating out the polar lipid fraction (see FIG. 1, water-alcohol layer, F #2). Polar lipids can be obtained from the F #2 fraction by evaporation, and pigments can be obtained by evaporation of the F #3 fraction. The F #1 layer may contain an amount of chlorophylls and carotenoids, which can be removed by methods known to those skilled in the art, e.g., methods known for the production of edible oils. Examples of these methods include adsorption-filtration using silica gel, bleaching clays such as B80, T41, activated carbon, and others. As a result of the selective removal of chlorophyll from the F #1 fraction, in this embodiment, a largely clear to dark amber, including reddish, somewhat liquid to semi-solid oil can be obtained.

In an alternative embodiment, the method for production of a low chlorophyll content oil composition, the algal biomass or algal paste so obtained includes both polar and non-polar lipid fractions and also has a chlorophyll concentration. Polarity characteristics of the polar and non-polar lipid fractions of the biomass are used to segregate polar from non-polar components in the algal biomass, including substantially segregating the chlorophyll concentration with the non-polar lipid fraction. As illustrated in Example 2 below, additional steps include bleaching out substantially all the chlorophyll concentration from the non-polar containing fraction; and re-combining the polar and non-polar lipid fractions to produce the low chlorophyll-content oil composition.

In addition to the low chlorophyll-content aspect of the composition, the present invention also provides for isolated oil derived from algae which are rich in LC-PUFAs, including at least one Omega-3 fatty acid such as, but not limited to, EPA or DHA, at least partially in the form of whole and unhydrolyzed phospholipids and whole and unhydrolyzed glycolipids extracted by the above processes. The oil produced by such process is unexpectedly high in polar lipids such as phospholipids and glycolipids. It is known that krill oil, by virtue of the contained phospholipids (a polar lipid) has higher bioavailability in mammals than does fish oil, which comprises almost exclusively neutral lipids (triglycerides). See, Jan Philipp Schuchardt et al., *Lipids in Health and Disease* 2011, 10:145. Remarkably, the oils extracted from algae such as *Nannochloropsis* using the inventive methods showed bioavailability to mammals that surpassed even krill oil.

After isolation of the algal oil, incorporation of the algal oil into a medical formulation can occur. The active ingredient of the medical formulation can include, but is not limited to, a pharmaceutical drug, a vitamin or dietary supplement, other omega-3 containing oils, or an antioxidant. Incorporation of the isolated algal oil can, as non-limiting example, comprise means of direct mixing with the active ingredient, by incorporation with other excipients understood to provide an optimal dosage form, and by coating of components and surfaces of the dosage form with the algal oil or a mixture of algal oil and other excipient species. In one preferred embodiment, incorporation of isolated algal oil can be via the application of the algal oil to the exterior of a gel capsule, pill, tablet, or otherwise consumable dosage form, so as to increase the lipophilicity of the dosage form. The following examples are illustrative of the invention, both for clarifying and determining specific components of the oil composition, and for producing the LC-PUFA-rich and low-chlorophyll, low-polysaccharide-containing oils as further described herein:

EXAMPLES

Example 1

2.1 Process Protocol for this Example (as Referred to in FIG. 1)

1) 100 g of *Nannochloropsis* algal paste (22-27% of solids in water) was weighed out. (Stage 1, FIG. 1)

2) The algae paste was placed in a 2 L flask and 850 ml of alcohol was added. (Stage 1, FIG. 1)

3) The algae was extracted for 45 min at a temperature of 70° C. with vigorous stirring. (Stage 1, FIG. 1)

4) Solid algae residues were filtered out from the ethanol extract (vacuum filtration). (Stage 2, FIG. 1)

5) The ethanol extract from the previous stage was placed into a separatory funnel (2 L), 300 mL of heptane was added to the resulting extract, stirred vigorously for 2 min, the layers were separated, the top layer was carefully selected and placed in a separate flask and about 120 mL of a green heptane layer was obtained. (Stage 3, FIG. 1)

6) Another 100 mL of heptane was added to the ethanol layer, stirred vigorously for 2 min, the layers were separated (ethanolic layer—lower, and heptane layer—upper), the top layer was carefully selected and combined with the heptane layer obtained in the previous stage (~200-220 mL of combined green heptane layers was obtained, fraction F #1). (Stage 4, FIG. 1)

7) 1 gram of silica gel was added to the entire heptane layer obtained and, after vigorous stirring for 5 minutes, the slurry was filtered through a layer of one gram of silica gel (instead of silica gel, activated carbon or T41 bleaching clay can be used). Due to variations in the properties of various silica gels, activated carbons, and bleaching clays, the actual amounts of the materials should be adjusted on plant. (Stage 8, FIG. 1)

8) The lower (ethanolic) layer was taken from this protocol stage 6, 350 mL of water and 200 mL of heptane were added, and the mixture was shaken intensively for 2 mins. After about 5 min of settling the separate phases, the top layer was carefully selected and placed in a separate flask (~400 mL of a green heptane layer was obtained at this stage). (Stage 5, FIG. 1)

9) The lower layer was repeatedly extracted from the above stage with 200 mL of heptane (3×200 mL). The top layers were carefully selected and combined with the heptane layer obtained in the previous stage. (~1000-1020 mL of combined green heptane layers was obtained, fraction F #3). (Stage 5, FIG. 1)

10) The extracted lower layer contained clarified polar lipids (F #2). This fraction can be polished by 3 g of, e.g., Amaze-N bleaching sorbent, from Helix Chromatography (15 E. Palantine Rd. #118, Prospect Heights, Ill. 60070; helixchrom.com), (or similar sorbents can be used, if needed).

11) The fractions obtained were evaporated in vacuum with heating <45° C.

Figure 4:
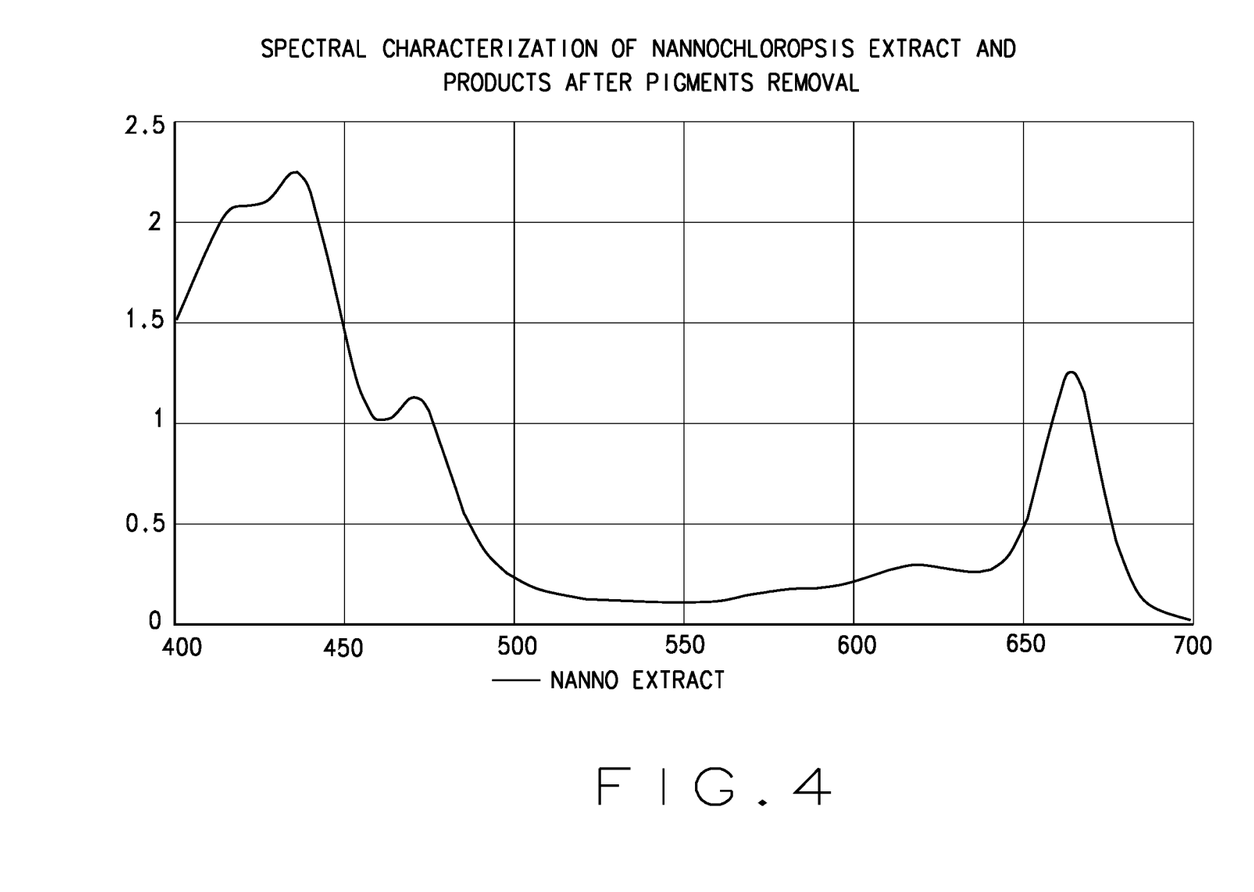
FIG. 4 is a graphical depiction of a spectral characterization of an embodiment of an ethanolic extract of *Nannochloropsis* and products after pigments removal as discussed in Example 1. Y axis=AU (optical Absorption Units), X axis=nm (nanometers, wavelength).

The above process steps and experimental results demonstrate a highly efficient exemplary method for a liquid-liquid extraction, removing chlorophyll and a fraction of carotenoids from phototrophic (autotrophic) algal extracts, such as for *Nannochloropsis* or *Chlorella* lipids. By use of the above embodiment of a method of the disclosure, more than 99% of chlorophylls $\alpha$ and $\beta$, and pheophytins were removed from an ethanolic extract of *Nannochloropsis* (EEN), as well as about two-thirds of the carotenoids (medium polarity carotenoids). In doing so, at least 90 weight %, preferably greater than 95 weight %, more preferably greater that 97.5 weight %, even more preferably greater than 98.0 weight %, and most preferably, greater than 99 weight % of the original mass balance is fully retained and can be characterized as to its principal component parts without resorting to leaving a large portion of the mass balance as simply being uncharacterized or characterized only "by subtraction" or "by difference". See Table 1: Extraction mass balance (composition) and Table 2: Principal components of the ethanolic extract of *Nannochloropsis* for mass and weight % analysis of the compositions. (Representing 99.86% of the total algal biomass by weight %.) See FIG. 4 for a spectral characterization of the *Nannochloropsis* ethanolic extract after removal of pigments.

TABLE 1

Extraction mass balance (composition)
Extraction Mass Balance

| Item | Value |
|---|---|
| Algal paste concentration, % | 27.5% |
| Initial paste mass, g | 100.0 g |
| Solid mass (recalculated), g | 27.5 g |
| Extract volume, mL | 950 |
| Extract mass, g | 9.97 |
| Concentration (mg/mL) | 10.5 |
| Extract mass, % | 36.25 |
| Residue mass, % | 63.75 |

TABLE 2

Principal components of the ethanolic extract of *Nannochloropsis*
Principal groups of components

| Item | Mass, g | Weight % |
|---|---|---|
| Non-polar lipids | 1.533 | 15.36 |
| Medium polarity lipids | 2.605 | 26.09 |
| Chlorophyll total | 0.697 | 6.98 |
| Carotenoids total | 0.223 | 2.23 |
| Polar lipids | 3.62 | 36.23 |
| Sugars and polar components | 1.294 | 12.97 |
| Total: | 9.951 | 99.86 |

While viscosity measurements can vary to a degree depending on such factors as temperature, compositional concentrations of various ingredients in a formulation, etc., a viscosity reading taken for an embodiment of a *Nannochloropsis* extract prepared as described after combination of a polar lipids fraction with a neutral lipids fraction at 25° C. as described herein was noted to be @ 165,000 mPa·s.

In summary, the products shown in Example 1 can be broken down into three principal fractions of the incoming ethanolic extract of *Nannochloropsis* (EEN)—1) Fraction (F #1), non-polar lipids, mainly triglycerides; 2) Fraction (F #2), polar lipids, including glycolipids and phospholipids; and Fraction (F #3), a fraction of medium polarity, comprising di- and mono-glycerides, free fatty acids (FFA's), carotenoids and chlorophyll. The clarified F #1 and F #2 fractions can be used as sources of valuable lipids high in palmitoleic and eicosapentaenoic acids (EPA). F #3, as a concentrate of natural pigments, including chlorophyll, astaxanthin, zeaxanthin, and others, also have value as food additives. Fractions F #1-3 can each be used as food additives and are valuable raw materials with high biological potential.

Example 2

A sample of a dark green paste of the algal biomass was prepared generally in accordance with a method outlined in U.S. Pat. No. 8,591,912 B1 (see, generally, Col. 6, line 62 to Col. 9, line 3) and discussed herein (see, e.g., at [0025]). The algal biomass paste was extracted with hot absolute ethanol. Specifically, 66 g algal paste, 3×250 mL ethanol, at 75° C., 30' while stirring at 500 rpm each, centrifugal separation at 4450 rpm for 10 minutes, yielded a specimen algal extract.

An analysis conducted of the oil extract demonstrated the principal polar lipids in the algae specimen to be: 1) glycolipids (monogalactosyl diglycerides (MGDG) and digalactosyl diglycerides (DGDG) and 2) phospholipids (phosphatidlycholine, phosphatidylethanolamine, and phosphatidylinositol) (See Table 3, herein.)

TABLE 3

| Item | Mass, g | Weight, % | Group |
|---|---|---|---|
| Sample mass (wet algae paste) | 66.1 | n/a | Quantification |
| Dry algae (calculated) | 15.87 | 100 | Quantification |
| Dry* residue after extraction | 9.32 | 58.7 | Quantification |
| Crude extract mass | 6.56 | 41.3 | Quantification |
| Non-Lipid Components | 1.95 | 12.3 | Components |
| Non-polar lipids** | 1.11 | 7 | Lipids |
| Glycolipids*** | 1.76 | 11.1 | Lipids |
| Phospholipids**** | 0.78 | 4.9 | Lipids |
| Chlorophyll | 0.75 | 4.74 | Pigments |
| Carotenoids | 0.21 | 1.33 | Pigments |

*permanent weight on drying at room temperature (final moisture was not tested)
**TAG, DAG, FFA, Phytosterols
***Glycolipids (AMGDG, MGDG, DGDG, SQDG)
****Phospholipids (PC, PE, PI, PA, PG)

An embodiment of a bioavailable, low chlorophyll content, polar lipids-rich, LC-PUFA-rich, Omega-3 oil rich oil of the disclosure as quantified herein was prepared from the above starting material using the following additional steps:

1) Polar lipids were separated from a mixture of non-polar lipids, chlorophylls, and other components based on differences in polarity.

2) Chlorophylls were bleached from the remaining non-polar lipid components using well developed protocols for vegetable oil bleaching generally as described in Example 1 above; and e.g. 1 gram of silica gel was added to the entire heptane layer obtained and, after vigorous stirring for 5 minutes, the slurry was filtered through a layer of one gram of silica gel (instead of silica gel, activated carbon or T41 bleaching clay can be used). Due to variations in the properties of various silica gels, activated carbons, and bleaching clays, the actual amounts of the materials should generally be adjusted on plant.

3) The polar lipids fraction of (1) above was combined with the bleached non-polar lipids of (2) above.

Figure 5:
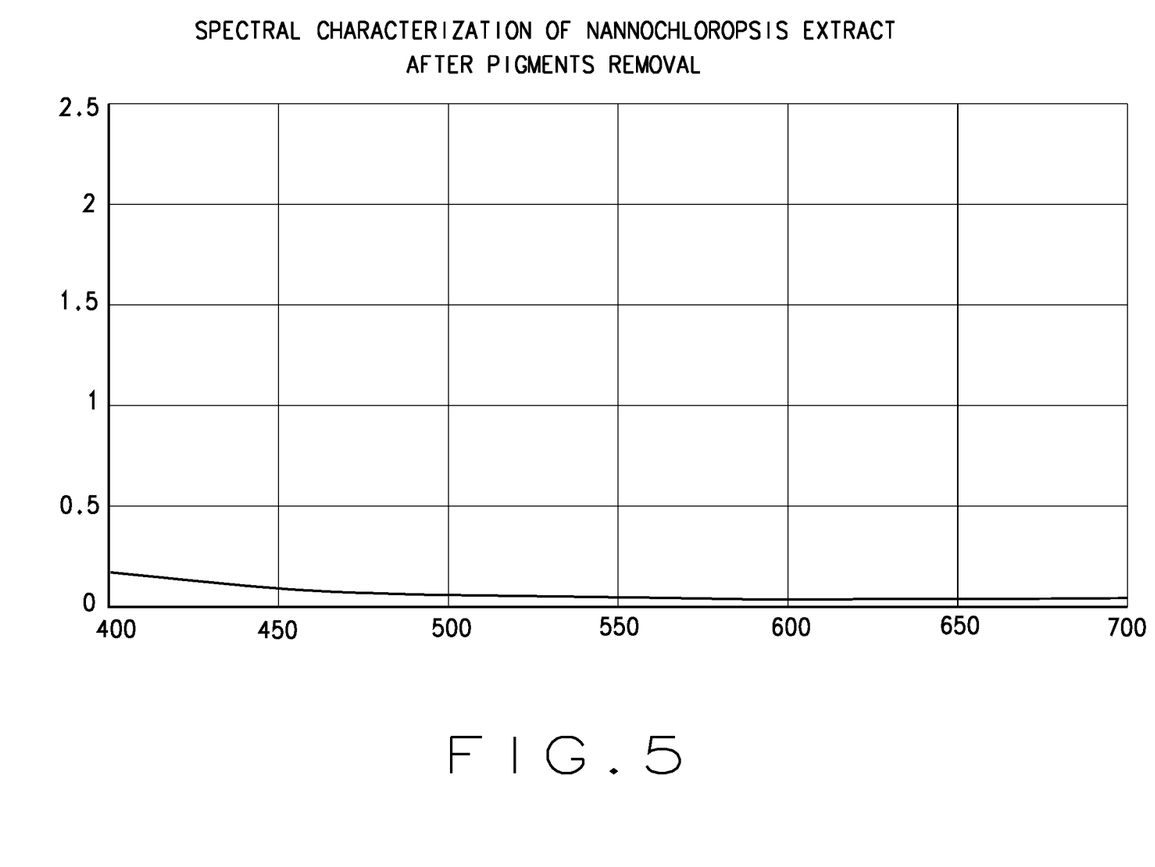
FIG. 5 is a graphical depiction of a UV-Visible spectral characterization of an embodiment of an algal extraction as discussed in Example 2. Y axis=AU (optical Absorption Units), X axis=nm (nanometers, wavelength).

A bioavailable polar lipid-rich, low chlorophyll-containing oil composition having a generally low viscosity and with a nearly clear to light brown color was obtained. See FIG. 5 for spectral analysis. The composition was a waxy solid at ambient temperature of @ 70 degrees Fahrenheit. The composition melts when warmed and exhibits low viscosity when blended with other oils such as triglycerides and the like.

An analysis of the oil composition of embodiments of the bioavailable oil of the disclosure made using the above processes described herein demonstrated that oils having the following components and features (column 1), and component ranges (column 2), as set forth in Table 4 were obtained from algal biomass:

TABLE 4

|  | Components/Features of Exemplary Composition | Ranges of Components of Disclosed Compositions |
|---|---|---|
| Total Lipid concentration in the oil product | >90% | >75% |
| Polar Lipid fraction of lipids | ~70% | >20% |
| Total Omega 3 content in oil product | ~30% | >20% |
| Total EPA content in the oil product | ~30% | >20% |

TABLE 4-continued

| Components/Features of Exemplary Composition | Ranges of Components of Disclosed Compositions |
|---|---|
| Glycolipid concentration as % of polar lipid | ~60% | >30% |
| Glycolipid as % of oil product | ~40% | >20% |
| Phospholipid as % of polar lipid | ~40% | >20% |
| Phospholipid as % of oil product | ~25% | >10% |
| Total chlorophyll concentration in oil product | <0.1% | <4% |
| Total polysaccharide content (%) in oil product | <1% | <4% |
| Color/Capacity? | Dark Amber - Clear | Dark Amber - Clear |

Modest variations in the weight % of components and other characteristics of the oil disclosed in this application may be obtained by alterations to the process employed, as is known to those skilled in this art. However, preferably the weight % of the polar lipid fraction of the total lipid concentration of the produced oil exceeds 20%, preferably exceeds 30%, more preferably exceeds 40%, even more preferably exceeds 50%, and still more preferably is about 70% or above. Also, preferably, the weight % of the chlorophyll concentration in the oil product is less than 4% of the weight of the total oil product, more preferably, it is less than 3.0%, yet more preferably, it is less than 2.0%, even more preferably, it is less than 1.0%, 0.75%, 0.50%, 0.2% and still more preferably, it is 0.1% or below. Also, preferably, the weight % of the polysaccharides concentration in the oil product is about 4% or less of the weight of the total oil product, more preferably, it is less than 3.0%, yet more preferably, it is less than 2.5%, 2.0%, even more preferably, it is less than 1.0%, 0.5% or below. Additionally, the weight % of glycolipids as a weight % of total polar lipids exceeds 20%, preferably exceeds 30%, more preferably exceeds about 40%, even more preferably exceeds 50%, 60%, 70% and still more preferably it is 80% or above, and its weight % of the total oil composition exceeds 10%, more preferably 20%, and still more preferably is about 25% or above. Additionally, the weight % of phospholipids as a weight % of polar lipids exceeds 20%, more preferably exceeds 30%, and still more preferably exceeds 35%, and their weight % of the total oil composition exceeds 20%, more preferably 30%, and still more preferably 40%. While not being bound by any particular theory, applicant believes that by the combination of these characteristics, including very low chlorophyll concentration in the oil product, an attractive, lightly colored, nearly clear, to amber, up through darker amber color is produced, and in a preferred embodiment, nearly clear to amber. Also, EPA concentration of the total oil product content is at least 20 weight %, more preferably at least 25%, and still more preferably at least about 30 weight % or greater is produced. Similarly, the Omega-3 content of the oil product is at least 20 weight %, more preferably at least 25 weight %, and still more preferably at least 30, 40 weight % or greater is produced. Considered as a whole, the weight % of LC-PUFA content of the oil product at least 20%, at least 25%, 30%, 40% and 50%.

Elevated bioavailability of the resultant oil is also achieved. Moreover, unlike some prior art methods of extracting and fractionating microalgae, the disclosed method does not involve aggressive chemistry such as the use, e.g., of strong mineral acids which frequently destroy polar lipids and can significantly degrade other valuable fractions of the algal biomass.

Figure 3:
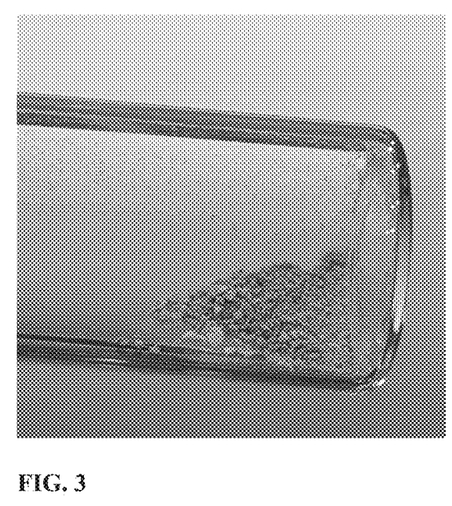
FIG. 3 is a photographic depiction of a powder obtained by an embodiment of a process of the disclosure made up substantially of non-lipids components comprising, e.g., polysaccharides contained in the crude ethanolic algal extract made according to an embodiment of the process as described herein.

Also obtained in embodiments of processes of the disclosure are powders of non-lipids components such as polysaccharides of the crude ethanolic algal extracts. See FIG. 3.

It should also be noted that for LC-PUFA, Omega-3, EPA-containing, high polar content oils of the disclosure, there is a greatly reduced weight % of the following chlorophylls: 1) chlorophyll a, 2) protochlorophyll a, and 3) methylchlorophyllide. Preferably, the weight % of the chlorophylls of the composition is less than 4%, preferably less than 3%, yet more preferably less than 2%, even more preferably less than 1%, still more preferably less than 0.5%, 0.5%, and still even more preferably less than 0.1% of the total weight % of the composition.

In another embodiment of a composition of the disclosure, the composition has an enhanced weight % of several other ingredients, including carotenoids, e.g., carotenes (α and β), and zeaxanthins (yellow pigments), and canthaxanthin and zeaxanthin (reddish pigments), with total carotenoids making up more than 0.5% of the total weight of the extract and preferably more than 1%.

In other alternative embodiments of the disclosure, the bioavailable, high polar-lipids containing, EPA-containing, low chlorophyll content oil compositions, embodiments of which are disclosed herein, can be presented as formulations in which other useful ingredients are added. These other useful ingredients can be added alone, or in one or more combinations, e.g., combinations with other essential oils, dietary supplements, health supplements and the like. Specific examples include, but are not limited to—1) other omega 3 containing oils or components such as DHA and EPA (e.g., in the form of the neutral lipids extracted as a product in the instant invention or externally sourced), the lysolipids from the instant invention, or externally sourced, ethyl esters of DHA or EPA; 2) antioxidants such as carotenoids, including astaxanthin, lutein, zeaxanthin, lycopene, carotenes (alpha and beta), cryptoxanthin, and mixture thereof (including the carotenoid fraction of the instant invention); 3) vitamins, such as vitamin C and D; 4) cannabinoids, such as cannabidiol (CBD), and 5) other combinations. It is understood that such formulations including some of these species with less-colored and/or less-viscous compositional profiles, may reduce the overall color profile and viscosity of formulations which include the fatty acid compositions with high polar lipid, high glycolipid, and low chlorophyll concentrations prepared by embodiments of the processes disclosed herein. Thus, this may be achieved, e.g., by inclusion of non-polar lipids, either added back in from original biomass stock, or from an external source, or by preparation of formulations which demonstrate such attributes.

Examples of nutraceutical formulations including blends of the polar EPA fraction described above with DHA (Omega-3) can beneficially be in a ratio from 10-90 to 90-10, wherein preferable levels of the polar EPA formulation component being mixed at 20-50%. Uses for such formulations include both use as a key food supplement/nutraceutical in its own right for cardiovascular health, mood, anti-depression and more, and also as a delivery system for other neutral lipids and components it is formulated with. This can be DHA, other neutral forms of EPA, or mixtures thereof. Astaxanthin at levels of 0.04% TO 10%, preferably 0.1% to 2%, and more preferably 0.2% to 1% can also be beneficially formulated, either with pure polar EPA lipids or blends thereof with neutral EPA and/or EPA. Another component that could be beneficially added to such a formulation is coenzyme Q10 at levels of around 1-50%, preferably about 2-20% on the polar EPA, either pure or in any of the above formulations.

In addition to other attributes, formulation blends with added neutral lipids, e.g., can be useful to target various viscosity levels, such as 50,000 cps, preferably less than 10,000 cps, more preferably less than about 2,000 cps, and most preferably, about 300 cps or less.

In view of the above, it will be seen that the several objects and advantages of the present disclosure have been achieved and other advantageous results have been obtained.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A composition comprising a concentration of total lipids, wherein at least 20% of the total lipids concentration by weight % comprises a polar lipids fraction, with greater than about 30% by weight % of the polar lipids fraction comprising glycolipids, and wherein the composition comprises no greater than 1.0% of its weight % as chlorophyll concentration, wherein the composition has a clear to dark amber color.

2. The composition of claim 1 wherein the composition has a concentration of total lipids of at least about 75% by weight % of the composition as a whole.

3. The composition of claim 1 wherein the composition has a concentration of total lipids of at least about 90% by weight % of the weight % of the composition as a whole.

4. The composition of claim 1 wherein at least about 50% of the total lipids concentration by weight % comprises a polar lipids fraction.

5. The composition of claim 1 wherein the composition further comprises at least about 20% by weight % total omega 3.

6. The composition of claim 5 wherein the weight % of total omega 3 of the composition comprises at least about 30% by weight %.

7. The composition of claim 1 wherein the composition further comprises at least about 20% by weight % total EPA.

8. The composition of claim: 1 wherein the glycolipids comprise at least about 60% as a weight % of its polar lipids.

9. The composition of claim 1 wherein the composition comprises at least about 20% glycolipids by weight.

10. The composition of claim 1 wherein the composition comprises at least about 40% glycolipids by weight.

11. The composition of claim 1 wherein the composition further comprises phospholipids as a weight % of its polar lipids, comprising at least about 40% by weight of its polar lipids.

12. The composition of claim 11 wherein the phospholipids comprise at least about 60% by weight of its polar lipids.

13. The composition of claim 1 wherein the composition comprises at least about 20% by weight phospholipids.

14. The composition of claim 13 wherein the composition comprises at least about 40% by weight phospholipids.

15. The composition of claim 1 wherein the composition comprises no more than about 4% by weight polysaccharides.

16. The composition of claim 15 wherein the composition comprises no more than about 2% by weight polysaccharides.

17. The composition of 1 wherein the composition: is characterized by having a viscous to waxy oil texture at 70 degrees F.

18. A composition comprising a concentration of total lipids, wherein at least 50% of the total lipids concentration by weight % comprises a polar lipids fraction; wherein the polar lipids fraction comprises at least 40% glycolipids as a weight % of its polar lipids fraction and wherein the composition comprises no greater than 1.0% of its weight % as a chlorophyll concentration, wherein the composition has a clear to dark amber color.

19. The composition of claim 18 wherein the total composition comprises at least about 20% glycolipids by weight.

20. The composition of claim 19 wherein the total composition comprises at least about 40% glycolipids by weight.

21. The composition of claim 18 wherein the composition has a concentration of total lipids of at least about 75% by weight % of the composition taken as a whole.

22. The composition of claim: 21 wherein the composition has a concentration of total lipids of at least about 90% by weight % of the composition taken as a whole.

23. The composition of claim 18 wherein at least about 70% of the total lipids concentration by weight % comprises a polar lipids fraction.

24. The composition of claim 18 wherein the composition further comprises at least about 20% by weight % total Omega 3.

25. The composition of claim 24 wherein the weight % of total Omega 3 of the composition comprises at least about 30%.

26. The composition of claim 18 wherein the composition further comprises at least about 20% by weight % total EPA.

27. The composition of claim 18 wherein the composition further comprises phospholipids of at least about 40% by weight of its polar lipids.

28. The composition of claim 27 wherein the phospholipids comprise at least about 60% as a weight % of its polar lipids.

29. The composition of claim 18 wherein: the composition comprises at least about 20% by weight % phospholipids.

30. The composition of claim 29 wherein the composition comprises at least about 40% by weight % phospholipids.

31. The composition of claim 18 wherein the composition comprises no more than about 4% by weight % polysaccharides.

32. The composition of claim 31 wherein the composition comprises no more than about 1% by weight polysaccharides.

33. The composition of claim 18 wherein the composition has a viscous to waxy oil texture at 70 degrees F.

34. A formulation comprising:
   a composition comprising a concentration of total lipids, wherein at least 20% of the total lipids concentration by weight % comprises a polar lipids fraction, with greater than about 30% by weight % of the polar lipids fraction comprising glycolipids, and wherein the composition comprises no greater than 1.0% of its weight % as chlorophyll concentration; and,
   one or more additives selected from the group consisting of:
   Omega 3 containing oils, antioxidants, vitamins, and minerals, wherein the composition has a clear to dark amber color.

35. The formulation of claim 34 wherein the antioxidant is selected from the group consisting of astaxanthin, lutein, zeaxanthin, lycopene, alpha carotene beta carotene, ubiquinone, and cryptoxanthin.

36. The formulation of claim 35 wherein astaxanthin and is present as 0.04% to 10% of the formulation.

37. The formulation of claim 35 wherein ubiquinone is present as 1-50% of the formulation.

38. The formulation of claim 34 wherein the one or more additives is DHA.

39. The formulation of claim 34 wherein the one or more additives is ALA.

40. The formulation of claim 34 wherein the composition of the formulation comprises no greater than 0.1% of its weight % as chlorophyll concentration.

41. The formulation of claim 34 wherein the vitamins are selected from the group consisting of: vitamin A, beta carotene, vitamin B1, vitamin B2, vitamin B3, vitamin B5, vitamin B6, vitamin B7, vitamin B9, vitamin B12, vitamin C, vitamin D2, vitamin D3, vitamin E, vitamin K, and choline.

42. The formulation of claim 34 wherein the minerals are selected from the group consisting of: calcium, phosphorus, potassium, sodium, magnesium, sulfur, iron, chlorine, cobalt, copper, zinc, manganese, molybdenum, iodine, and selenium.

43. A medical composition comprising:
a composition comprising a concentration of total lipids, wherein at least 20% of the total lipids concentration by weight % comprises a polar lipids fraction, with greater than about 30% by weight % of the polar lipids fraction comprising glycolipids, and wherein the composition comprises no greater than 1.0% of its weight % as chlorophyll concentration; and,
one or more additives selected from the group consisting of:
Omega 3 containing oils, antioxidants, vitamins, and minerals, wherein the composition has a clear to dark amber color.

44. The medical composition of claim 43 wherein said composition is in swallowable form.

45. The medical composition of claim 43, wherein said composition is in chewable form.

46. The medical composition of claim 43 wherein said composition is in dissolvable form.

47. The medical composition comprising of claim 43 wherein the concentration of total lipids is present on the exterior surface of the medical composition.

48. The formulation of claim 35 wherein ubiquinone is present as 2-20% of the formulation.

* * * * *